(12) United States Patent
Kurtz et al.

(10) Patent No.: US 6,391,020 B1
(45) Date of Patent: May 21, 2002

(54) PHOTODISRUPTIVE LASER NUCLEATION AND ULTRASONICALLY-DRIVEN CAVITATION OF TISSUES AND MATERIALS

(75) Inventors: Ron Kurtz; Gregory John Roy Spooner; Douglas L. Miller, all of Ann Arbor, MI (US); Alun Roy Williams, Wales (GB)

(73) Assignee: The Regents of the Univerity of Michigan, Ann Arbor, MI (US)

( * ) Notice: Subject to any disclaimer, the term of this patent is extended or adjusted under 35 U.S.C. 154(b) by 0 days.

(21) Appl. No.: 09/413,508

(22) Filed: Oct. 6, 1999

(51) Int. Cl.$^7$ ................................................ A61B 18/18
(52) U.S. Cl. .......................................... 606/2; 606/2.5
(58) Field of Search ........................ 606/2, 2.5, 3, 10, 606/11, 13, 15–17; 607/1, 88–89; 128/24, 660.03, 898

(56) References Cited

U.S. PATENT DOCUMENTS

| | | | | |
|---|---|---|---|---|
| 4,960,108 A | * | 10/1990 | Reichel et al. | 128/24 |
| 5,219,401 A | * | 6/1993 | Cathignol et al. | 128/660.03 |
| 5,368,031 A | | 11/1994 | Cline et al. | 128/653.2 |
| 6,203,540 B1 | | 3/2001 | Weber | 606/15 |
| 6,238,386 B1 | | 5/2001 | Muller et al. | 606/10 |

* cited by examiner

Primary Examiner—Michael Peffley
Assistant Examiner—Pete J Vrettakos
(74) Attorney, Agent, or Firm—Fleshner & Kim, LLP

(57) ABSTRACT

A method and apparatus for processing a material creates a cavitation nucleus in a portion of the material by focusing optical radiation at the portion of the material and then causing mechanical disruption in another portion of the material adjacent the cavitation nucleus by subjecting the cavitation nucleus to ultrasound waves.

35 Claims, 8 Drawing Sheets

PHOTODISRUPTIVE LASER NUCLEATION AND ULTRASONICALLY-DRIVEN CAVITATION OF TISSUES AND MATERIALS

This invention was made with Government support under NSF STC PHY 8920108 and NIH Grant CA42947. The Government has certain rights in the invention.

BACKGROUND OF THE INVENTION

1. Field of the Invention

The invention relates to processing of materials. More particularly, the invention relates to selectively destroying a portion of a material by using focused optical radiation and ultrasound waves.

2. Background of the Related Art

Both ultrasound and photodisruptive lasers have been used for material processing and tissue destruction. For example, ultrasound-driven phacoemulsification of the lens is a common surgical intervention in the eye, while Nd:YAG laser photodistruption of secondary cataracts is a common medical laser procedure. Destruction of a medium or tissue with ultrasound can be produced with sufficiently high powers such that absorption of the field heats the material directly and thereby destroys it. Alternatively, an inhomogeneity such as an inclusion, gas bubble or void can strongly couple to the ultrasound field, thereby mechanically destroying material in the vicinity of the inhomogeneity. In aqueous media, cavitation bubbles are commonly used to produce this effect. Finally, destruction of materials can be accomplished by direct mechanical vibrations, in which ultrasonic energy is transferred through a probe in a "jackhammer" fashion.

Phacoemulsification is a procedure that uses both cavitation and direct mechanical vibration in the lens of the eye by means of a probe, which also directs an acoustic field to drive these nuclei and produce a strong mechanical effect. This leads to emulsification of the lens material, which is subsequently aspirated and removed. In many materials, and especially tissues, cavitation nuclei are not normally present. In these cases, ultrasonic destruction of material must occur by the invasive introduction of nuclei, by direct ultrasonic absorption or by direct mechanical vibrations coupled into the material with a probe.

Various uses of lasers or ultrasound for destroying tissue are known in the art. For example, U.S. Pat. No. 4,960,108 discloses a method in which pulsed laser radiation situated in the infrared region is concentrated by means of an optical waveguide at a concrement to be destroyed which is surrounded with aqueous rinsing liquid. The concrement is destroyed mechanically by laser-induced breakdown of the rinsing liquid, giving rise to shock wave and cavitation. Ultrasound is not used in this method.

U.S. Pat. No. 5,582,578 discloses a method utilizing two shockwave pulses with a specified time delay and pressure relationship, the first shockwave pulse being used to induce a transient cavitation bubble cluster near the target concretion, and the second shockwave pulse to control and force the collapse of the cavitation bubble cluster towards the target concretion with concentrated energy desposition. The method does not involve the use of a laser. U.S. Pat. No. 5,800,365 shows a similar method.

Another method using only ultrasound is disclosed in U.S. Pat. No. 5,676,692. This method involves placing a reflector of ultrasound or an ultrasound energy conversion device which converts received ultrasound energy to heat adjacent the tissue to be treated. The use of lasers is not disclosed in the method.

A method involving the use of multiple ultrasound transducers is disclosed in U.S. Pat. No. 5,725,482. This method uses a plurality of standing compression waves established within the medium along corresponding longitudinal axes between opposing pairs of coordinated transducers. The target volume is located at the common intersection of the axes of the standing compression waves. This method does not involve the use of lasers.

U.S. Pat. No. 5,219,401 discloses an apparatus for selective destruction of cells by implosion of gas bubbles. The gas bubbles are created by cavitation provoked by an ultrasonic wave generator. Implosion of the gas bubbles results in destruction of cells situated adjacent to the imploded gas bubbles. The apparatus does not disclose creating a cavitation nucleus by focusing optical radiation.

The above references are incorporated by reference herein where appropriate for appropriate teachings of additional or alternative details, features and/or technical background.

SUMMARY OF THE INVENTION

Conventional systems and methods, including those discussed above, have various problems and drawbacks. For example, it can be difficult to precisely control the area of destruction with the known systems and methods. The present invention, among other things, remedies this problem.

The present invention includes a method of materials processing that includes the creation of a cavitation nucleus in a first portion of the material, or adjacent to the material, by focusing optical radiation at approximately the first portion of the material, or adjacent to the material, and causing mechanical disruption in a second portion of the material adjacent to the cavitation nucleus by subjecting the cavitation nucleus to ultrasound waves.

In particular embodiments of the invention, the optical radiation creates the cavitation nucleus by causing optical breakdown of the first portion of the material. In some of these embodiments, the optical radiation is sufficiently focused so that optical breakdown of substantially only the first portion of the material occurs.

In some embodiments, the optical breakdown results in the ionization of the first portion of the material.

In some embodiments, the optical radiation is a short pulse duration laser beam. In some of these embodiments, the pulse duration of the laser beam is between about 1 femtosecond and about 1 nanosecond.

In some embodiments, the frequency of the ultrasound waves is determined based on a size of the cavitation nucleus.

In some embodiments, the wavelength of the optical radiation is such that the material is transparent to the optical radiation.

In some embodiments, the laser beam has a wavelength of between about 400 nm and about $2\mu$.

In some embodiments, the optical radiation is directed to the first portion of the material by a fiber optic probe. In some of these embodiments, a sighting device is used to direct the fiber optic probe.

In some embodiments, the ultrasound waves are focused at or proximate the cavitation nucleus.

In some embodiments, the ultrasound waves cause a mechanical disruption in at most the first and second portions of the material.

In some embodiments, the second portion of the material is biological material and is destroyed, and a third portion of the material is not destroyed, the third portion of the material being that portion of the material other than the first and second portions of the material.

In some embodiments, protein is introduced into the material, the protein stabilizing the cavitation nucleus by surrounding the cavitation nucleus. Stabilization can also be achieved with lipids. The lipids may be introduced or already present in a particular material.

Particular embodiments of the invention include an apparatus for processing a material in accordance with the methods discussed above.

Some embodiments of the invention comprise a platform to which the optical radiation generator and the ultrasound transducer are mounted, wherein the material is a body of water and the apparatus is for producing a cavitation signature in the body of water.

Additional advantages, objects, and features of the invention will be set forth in part in the description which follows and in part will become apparent to those having ordinary skill in the art upon examination of the following or may be learned from practice of the invention. Objects and advantages of the invention may be realized and attained, in part, as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The present invention produces cavitation nuclei through, for example, the use of a short pulse duration laser beam focused into a material. The high intensity of the short duration laser pulse produces optical breakdown of the material at the focus, accompanied by the creation of a small acoustic cavitation nucleus. The wavelength of the laser is chosen such that the laser radiation is not substantially absorbed by the target material/tissue except at the focus of the laser beam. Materials/tissues so targeted are not significantly, and preferably not at all, effected or damaged by the laser except at the site of the optical breakdown. In the present invention, an ultrasound beam, which may be focused, is applied while the small cavitation nuclei or bubbles are present. Cavitation and mechanical disruption in the vicinity of the nuclei then occur. The cavitation nucleus can be formed in the material to be destroyed or it can be formed adjacent the material to be destroyed.

The results of the procedure described above is a non-invasive destruction of localized tissue, not possible with the ultrasound beam alone or the laser radiation alone. The invention can be used, for example, to produce lens emulsification without introducing an ultrasound probe. The conventional procedure of phacoemulsification requires a relatively large hole through the cornea to introduce the ultrasound probe. In addition, in ultrasound phacoemulsification, the capsule surrounding the lens may be damaged. With the present invention, it is believed that the lens capsule can be preserved and aspiration of the emulsified lens material can be accomplished through a very small needle.

While the invention will, at times, be discussed in relation to processing of an eye lens, it is applicable to the processing of any appropriate material.

Figure 1:
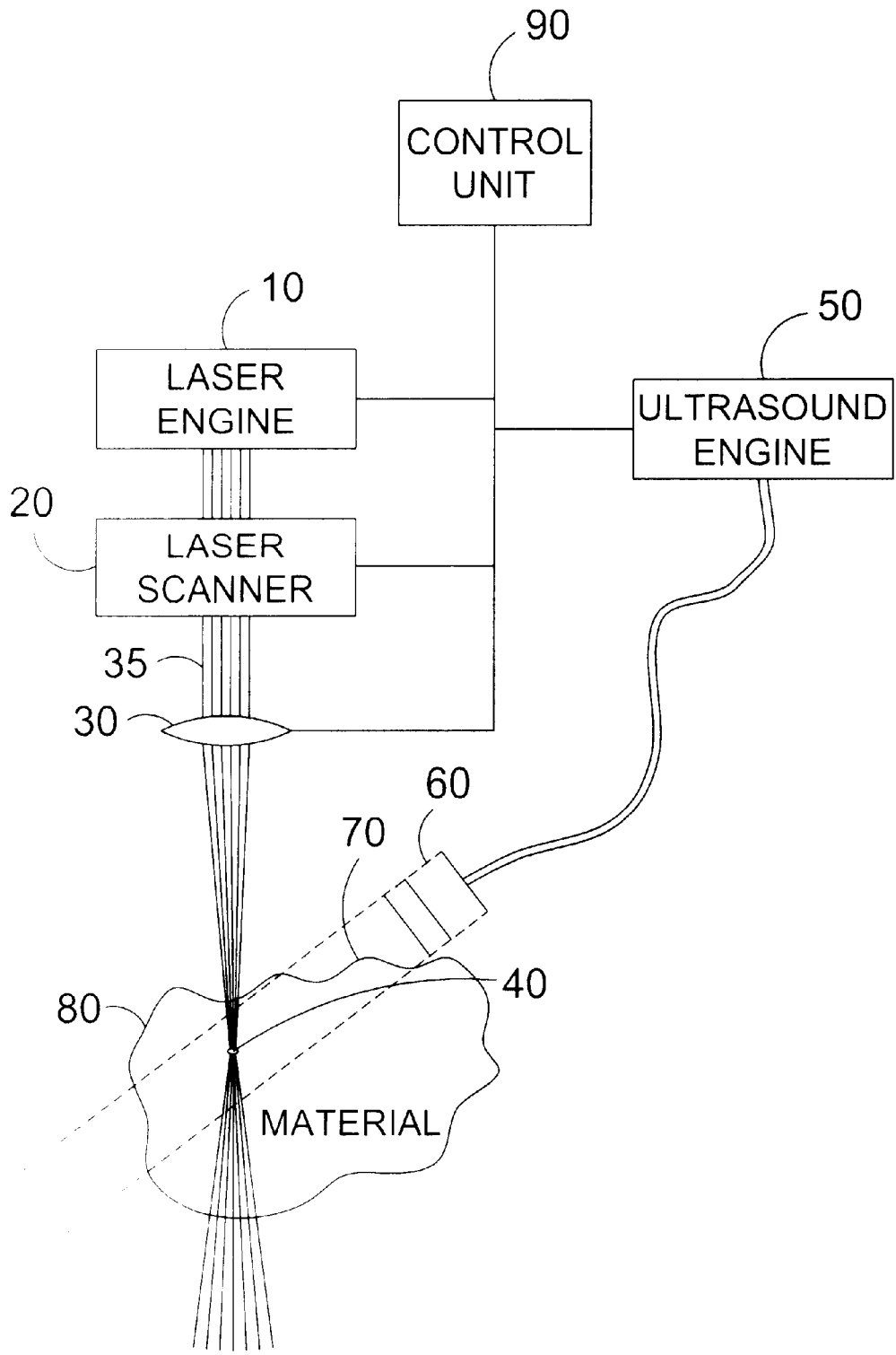
FIG. 1 is as schematic drawing of one embodiment of the invention.

FIG. 1 shows one embodiment of the invention. In FIG. 1, a laser engine 10 produces a laser beam that can be positioned in a plane perpendicular to the axis of the laser beam by a laser scanner 20. The focal point of the laser beam is then controlled by laser focusing optics 30. The focus 40 of the laser beam is positioned at the target area of the material 80. The laser beam is then pulsed, for example, by the laser engine 10 so that the portion of the material 80 at the focus 40 of the laser beam is ionized by the laser beam to create a plasma. The intense heat of the plasma vaporizes the material surrounding the plasma, creating a cavitation nucleus 45.

An ultrasound engine 50 in conjunction with an ultrasound transducer 60 produces an ultrasound beam 70. The ultrasound beam 70 is directed towards the material 80 such that the cavitation nucleus 45 is located in the ultrasound beam 70. Under the influence of the ultrasound beam 70, the gas inside the cavitation nucleus 45 expands, causing the cavitation nucleus to explode. The explosion of the cavitation nucleus 45 results in destruction of the material 80 in the vicinity of the cavitation nucleus 45. The laser engine 10, laser scanner 20, laser focusing optics 30 and ultrasound engine 50 are controlled by a control unit 90.

Figure 2:
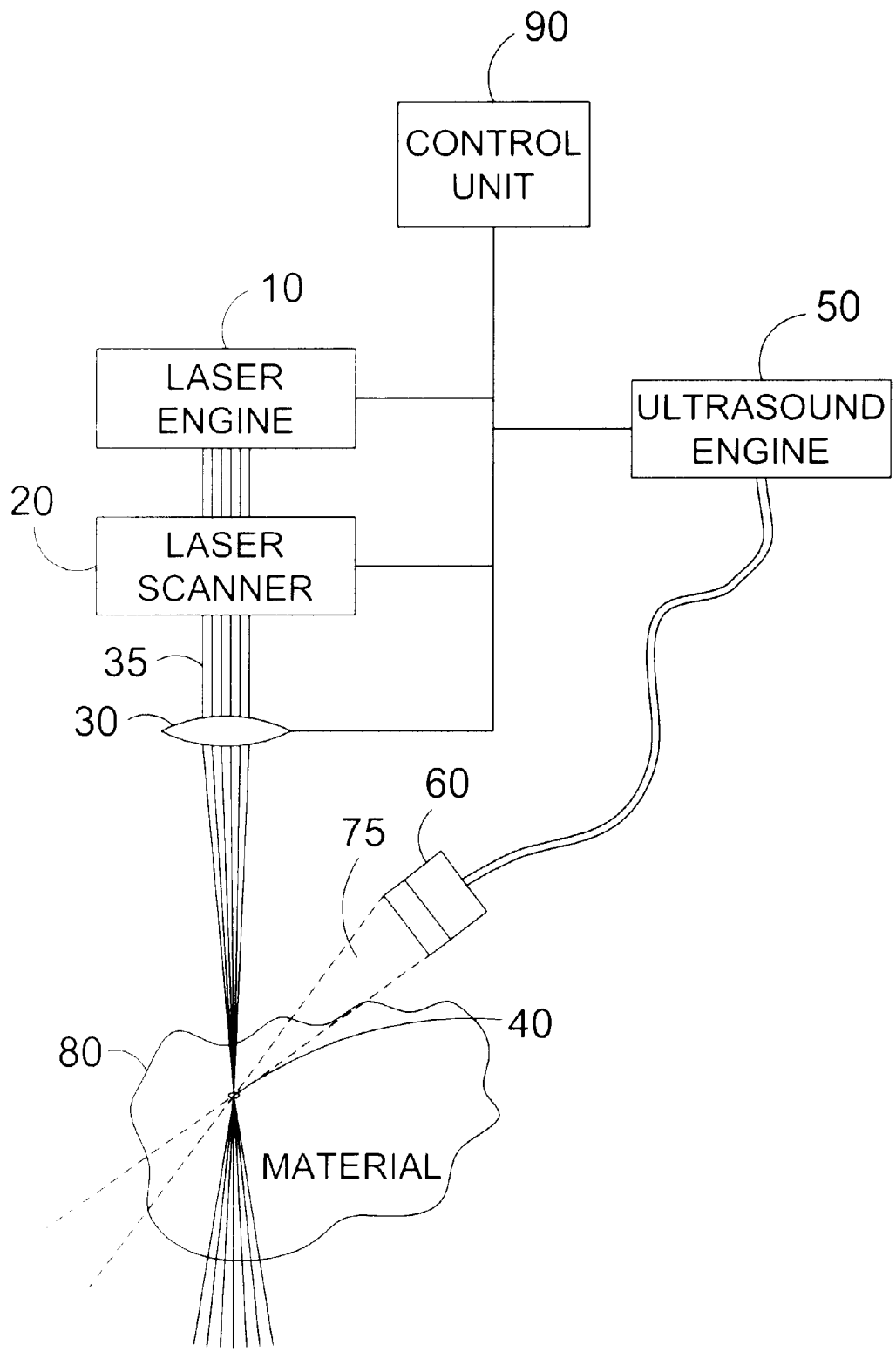
FIG. 2 is a schematic drawing of another embodiment of the invention.

FIG. 2 shows an embodiment of the invention similar to that of FIG. 1, except that the ultrasound beam 75 is focused and the laser beam and the ultrasound beam 75 are substantially confocal. By focusing the ultrasound beam 75, material 80 at locations other than the focus of the ultrasound beam 75 is subjected to a weaker ultrasound beam than is the cavitation nucleus 45. This embodiment reduces the chance of material 80 outside of the target area being damaged.

Figure 3:
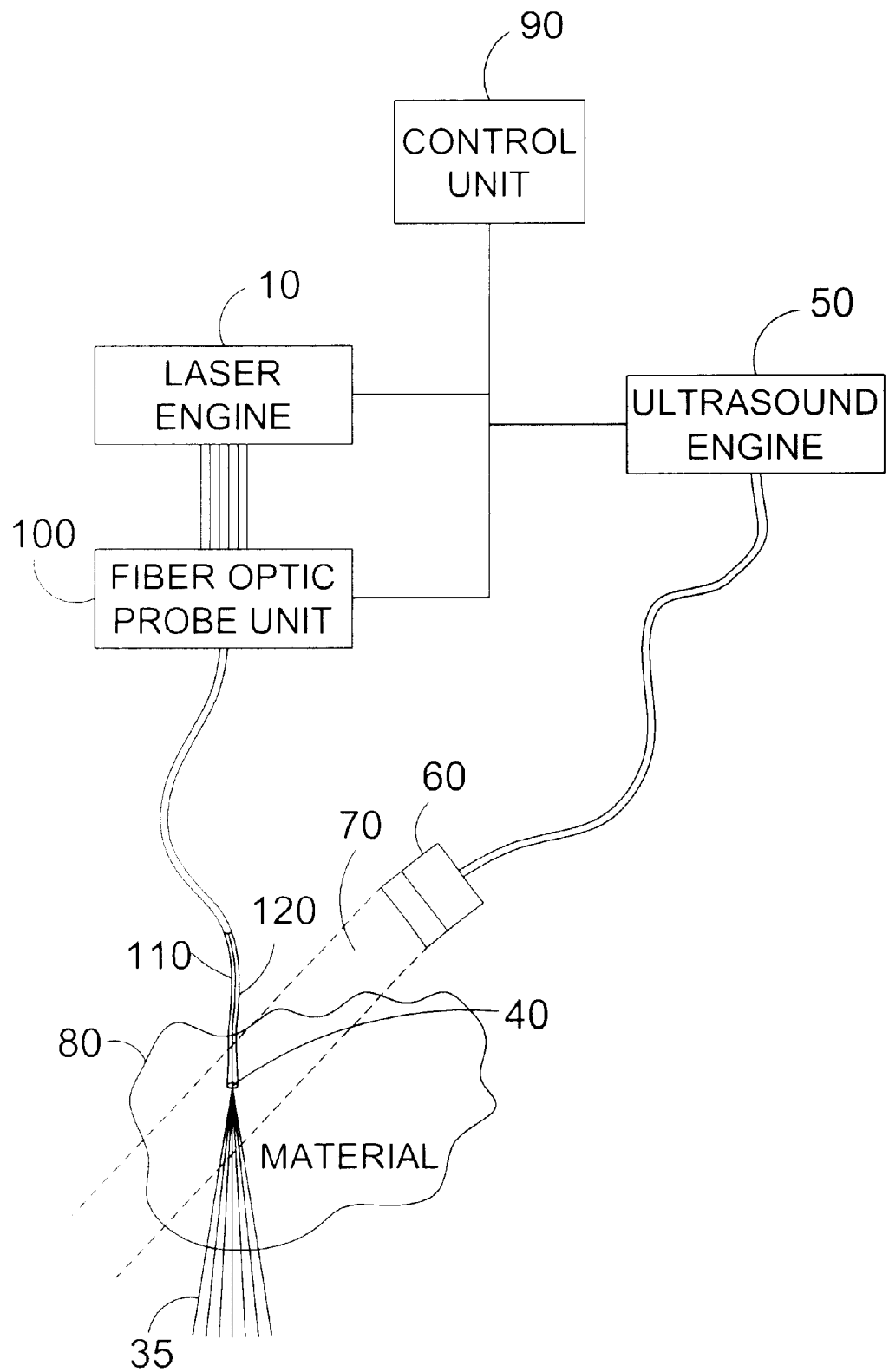
FIG. 3 is a schematic drawing of an embodiment of the invention using a fiber optic probe.
Figure 4:
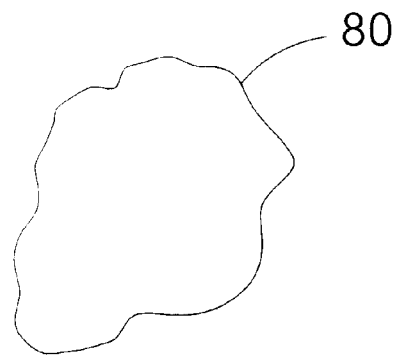
FIG. 4 shows a material prior to processing by the invention.

FIG. 3 shows an embodiment similar to that shown in FIG. 1, except that a fiber optic probe unit 100 and a fiber optic probe 110 are used to direct the laser beam to the target area. FIG. 3 also shows an optional sighting device 120 attached to the fiber optic probe 110 for use in positioning of the fiber optic probe 110. FIG. 3 shows an unfocused ultrasound beam 70. It is noted that at focused ultrasound beam, such as that shown in FIG. 2, can also be used. In addition, focusing optics (not shown) can be used in conjunction with fiber optic probe 110. Processing of the material will now be discussed in more detail with reference to FIGS. 4–7. FIG. 4 shows the material 80 prior to processing.

Figure 5:
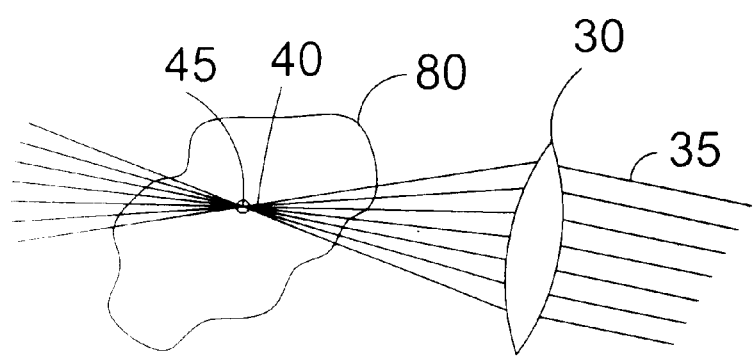
FIG. 5 shows the material of FIG. 4 during production of the cavitation nucleus.

FIG. 5 shows the laser beam 35 being focused by the laser focusing optics 30 at a focal point 40. The wavelength of the laser beam 35 is selected so that the material 80 is transparent or translucent to the laser beam 35 except at or near the focal point 40. The material 80 can be naturally transparent or translucent to the laser beam 35 or it can be made transparent or translucent by, for example, the application of drugs or other modifying processes. The intense concentration of the laser energy at the focal point 40 of the laser beam 35 ionizes the material 80 at the focal point 40 of the laser beam 35, and only at the focal point 40. The intense heat of the resulting plasma vaporizes the material 80 adjacent the plasma to create the cavitation nucleus 45, a bubble. The bubble size can be controlled by varying the energy of the laser pulse. A threshold energy is required for a given laser pulse width. Smaller bubbles require short pulses which have lower breakdown thresholds associated with them.

Figure 6:
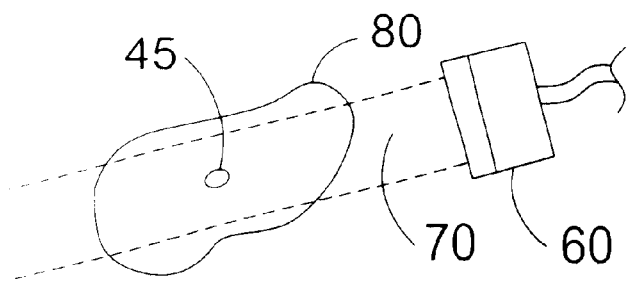
FIG. 6 shows the material and cavitation nucleus of FIG. 5 being subjected to ultrasound waves.

As shown in FIG. 6, the cavitation nucleus 45 is then subjected to the ultrasound beam 70, unfocused in this example but not necessarily unfocused. Under the influence of the ultrasound beam 70, the gases in the cavitation nucleus 45 are excited, causing explosion of the cavitation nucleus 45. The ultrasound beam 70 can be produced, for example, by a piezoelectric transducer, mechanical shock-wave generator, or other appropriate ultrasound wave generator. A wide range of excitations can be produced, from low-amplitude pulsation of the bubble, which might yield acoustic streaming around it, to high-amplitude implosion with jet formation, breakup into microbubbles, and general cavitational erosion processes, for example.

Figure 7:
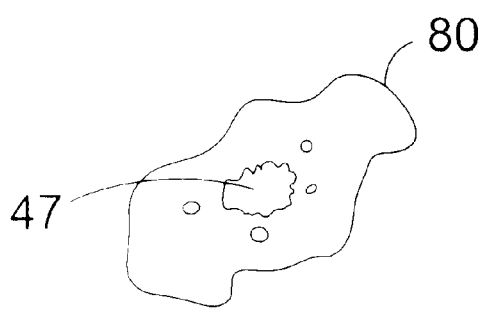
FIG. 7 shows the material of FIGS. 4–6 after processing by the invention.

FIG. 7 shows the condition of the material 80 after explosion of the cavitation nucleus 45. Processed portion 47 represents the portion of the material 80 that is processed, or destroyed, by the explosion of the cavitation nucleus 45.

The wavelength, pulse energy, pulse duration and pulse repetition of the laser beam must be determined based on the material to be processed. In the case of destruction of a portion of an eye lens, a wavelength of 1.06 microns, an energy of 10 microjoules, a pulse duration of 500 femtoseconds and a pulse repetition of 500 Hz has been found to be effective. Also, the optimum frequency, pulse duration, pulse repetition and pressure of the ultrasound beam can be determined for a particular material and cavitation nucleus size. As small bubbles sometimes exist in material to be processed, it can be important to select an ultrasound frequency that excites the cavitation nucleus (a relatively large bubble) but does not excite smaller bubbles existing in the material or unintentionally created by the laser beam. Experiments show that larger bubbles tend to have a lower resonant frequency than do smaller bubbles. In the case of destruction of a portion of an eye lens, a frequency of 3 MHz, a 2.5 ms pulse duration, a pulse repetition of 500 Hz and a pressure of 7.4 MPa has been found to be effective.

The material in which the cavitation nucleus is formed must be a material that can support a collapsible cavitation bubble. Common examples of such a material are liquids and gelatins. Also, other materials that are in semi-liquid states are appropriate, for example, some plastics. In addition, materials that are not liquids can be processed by arranging them to be in liquid. For example, a solid plate can be located in a liquid in order to etch a surface of the plate.

In order to prevent the cavitation nucleus from collapsing prematurely (i.e., before excitation by the ultrasound beam), proteins may be added to the material to envelop the cavitation nucleus. Such proteins, for example Albumin, have been shown to increase the duration in which the bubble exists and, therefore, lengthen the window of effective application of the ultrasound beam.

Other examples of medical procedures to which the invention is applicable are the destruction of collagen under the skin and "sculpting" by destruction of sub-dermal fat cells. In this application, it would not be necessary to remove the destroyed material and, therefore, the invention permits a completely non-invasive procedure.

Figure 8:
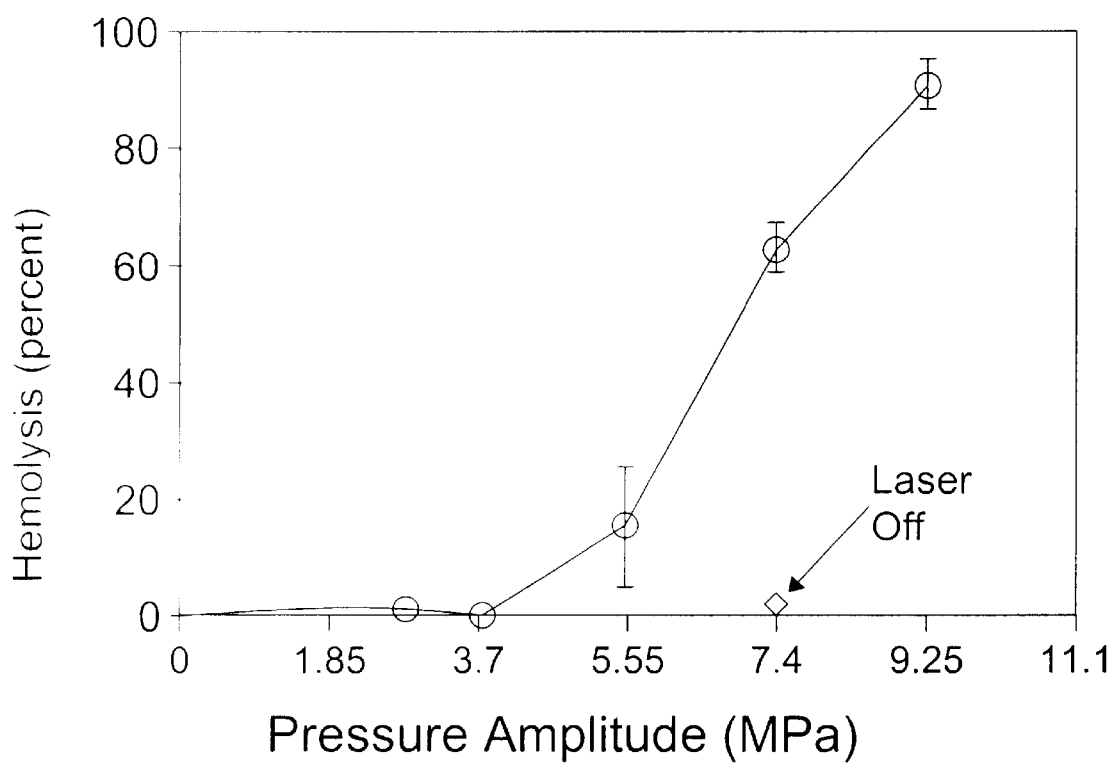
FIG. 8 is a graph showing the effect on hemolysis of ultrasound pressure amplitude and laser switching.

FIG. 8 shows the effect of ultrasound pressure amplitude on the lysis of canine red blood cells flowing through a confocal picosecond laser/ultrasound flow chamber. As can be seen from FIG. 8, as the ultrasound pressure amplitude is increased, a threshold is reached for the onset of cavitation breakdown of the red blood cells. Beyond the threshold, the effect increases approximately linearly with increasing ultrasound pressure amplitude. FIG. 8 also shows that switching the laser off (in this example, at a pressure amplitude of 7.4 MPa) eliminates essentially all hemolysis. In this experiment, the pulse energy of the laser was approximately 75 μJ, the laser rep rate was 500 Hz, and the focal spot size was approximately 10μ.

Figure 9:
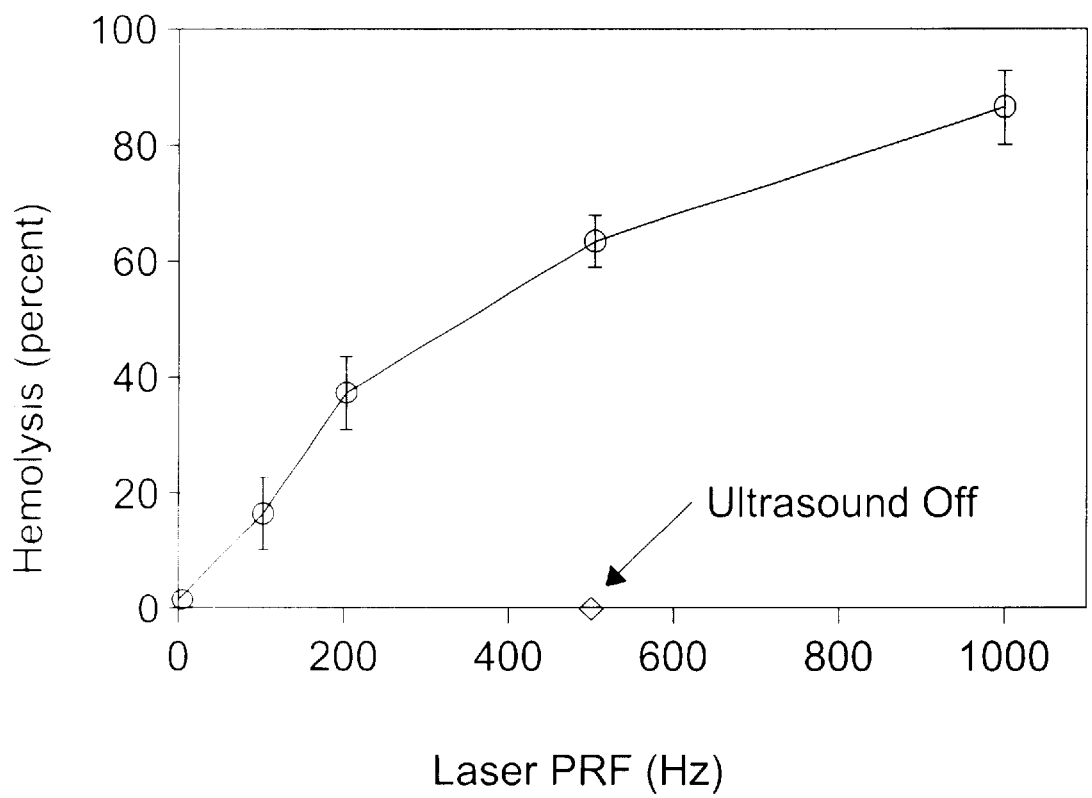
FIG. 9 is a graph showing the effect on hemolysis of ultrasound pressure amplitude and laser switching, laser rep rate and ultrasound switching.

FIG. 9 is similar to FIG. 8, except it shows hemolysis as a function of laser rep rate. In FIG. 9, as the laser rep rate is increased, the amount of hemolysis increases. The saturation effect shown in FIG. 9 at higher rep rates is apparently a result of a given flow rate through the flow chamber having a limit as to the number of usable cavitation events. As can be seen by the example at 500 Hz, switching off the ultrasound eliminates essentially all hemolysis. The same laser and ultrasound parameters were used in the experiment shown in FIG. 9 as in FIG. 8.

Figure 10:
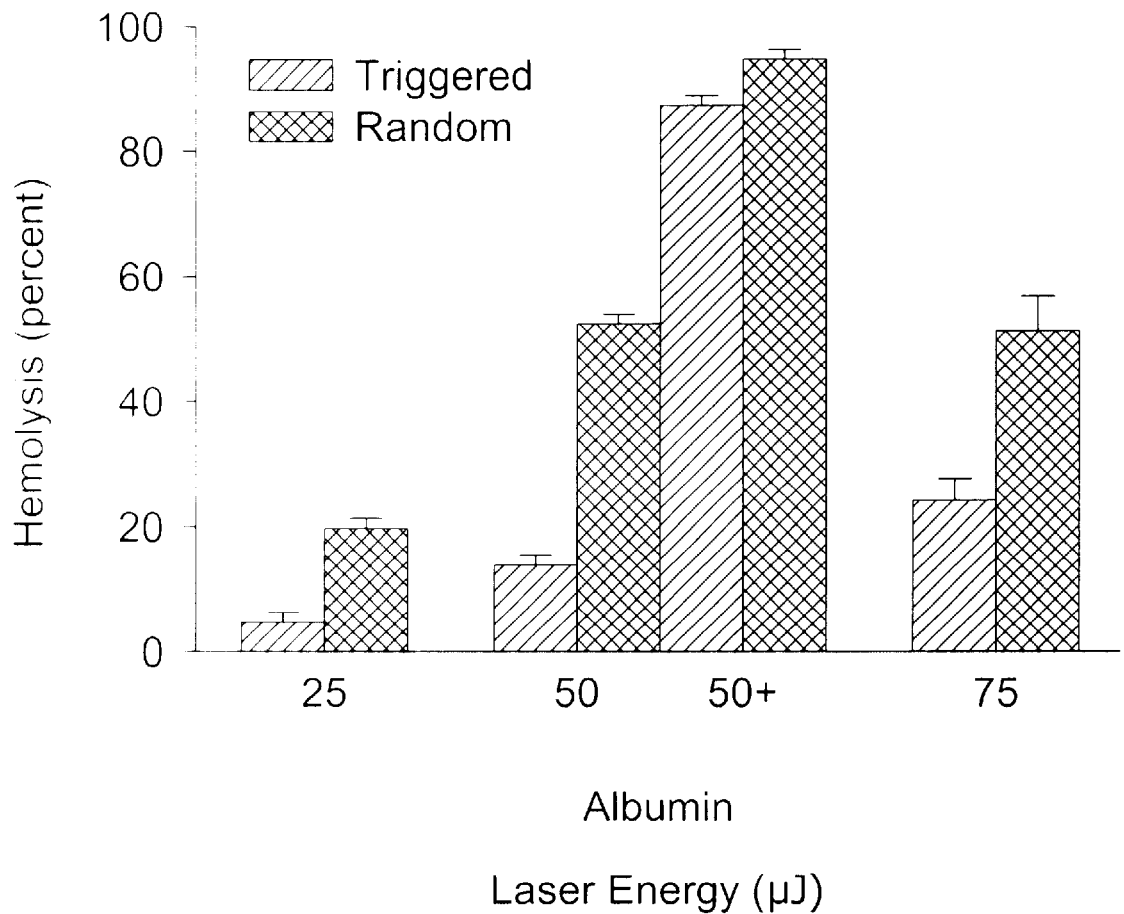
FIG. 10 is a graph showing the effect on hemolysis of triggering the ultrasound with the laser pulses and the effect on hemolysis of adding protein to the material.

FIG. 10 shows the effect of triggering the ultrasound with the laser pulses. In this experiment the ultrasound arrived at the focus approximately 24 μs after triggering due to the distance traveled between the transducer and the focus ((36 mm)/(1.5 mm/μs)). The lower hemolysis shown for triggered ultrasound compared to random ultrasound (at same rep rate as the laser) is apparently a result of the cavitation nuclei collapsing before being subjected to the ultrasound. In the case of unsynchronized triggering of the ultrasound, the ultrasound will, on average, be present more often than the triggered but delayed ultrasound when the cavitation nuclei are formed. FIG. 10 also shows the increased hemolysis that can result from adding protein to the material (50 μJ vs. 50 μJ+Albumin). It is noted that above a certain laser energy, the cavitation increase with energy levels off.

Experiments show that a certain amount of laser intensity is needed to produce the desired cavitation nuclei. Therefore, the desired effect can be achieved with less energy if the pulse width of the laser is reduced. However, some applications may be better served using conventional short pulse lasers instead of ultrashort pulse lasers.

Figure 11:
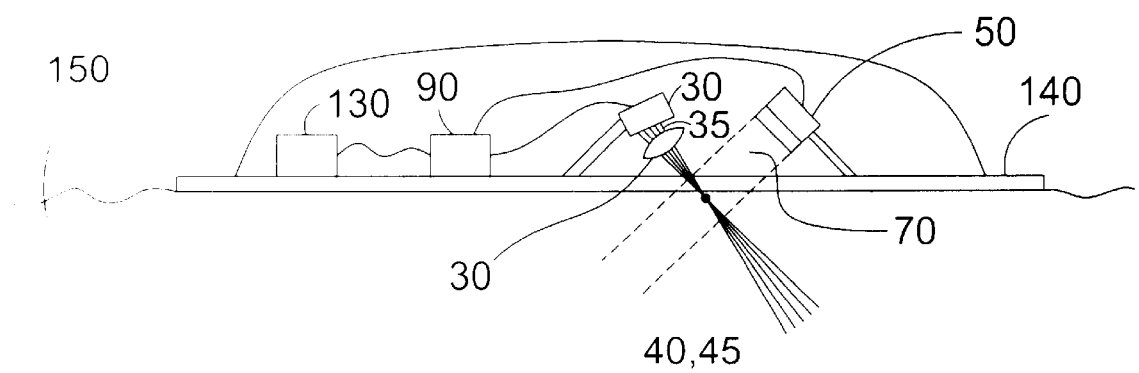
FIG. 11 shows an embodiment of the invention used to create a cavitation signature in a body of water.

FIG. 11 shows an example of another application of the invention. The apparatus shown in FIG. 11 generates a cavitation signature in a body of water in which the apparatus is located. The apparatus has a laser engine 10 which produces a laser beam 35 that is focused by laser focusing optics 30 such that the laser beam 35 is focused at focal point 40 to create cavitation nucleus 45 in body of water 150. Ultrasound engine 50 produces an ultrasound beam 70 to which the cavitation nucleus 45 is subjected. The excitation of the cavitation nucleus 45 by the ultrasound beam 70 causes the cavitation nucleus 45 to explode, thereby creating a cavitation signature in the body of water 150 that can be tuned to simulate the cavitation signature of a given ship, a military ship for example. The laser engine 10 and the ultrasound engine 50 are connected to a control unit 90 and a power supply 130. The entire apparatus is mounted on a platform 140. The apparatus can be used as a decoy in military situations to simulate a particular ship to sonar and other listening devices. The switchable nature of the invention aids in producing a tunable cavitation signature.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method of processing a first material, comprising:
   creating a cavitation nucleus in a portion of a second material by focusing optical radiation at approximately the portion of the second material; and
   causing mechanical disruption in a first portion of the first material adjacent to the cavitation nucleus by subjecting the cavitation nucleus to ultrasound waves.

2. The method of claim 1, wherein the optical radiation creates the cavitation nucleus by causing optical breakdown of the portion of the second material.

3. The method of claim 2, wherein the optical radiation is sufficiently focused so that optical breakdown of substantially only the portion of the second material occurs.

4. The method of claim 2, wherein the optical breakdown results in the ionization of the portion of the second material.

5. The method of claim 2, wherein the optical radiation is a short pulse duration laser beam.

6. The method of claim 5, wherein the pulse duration of the laser beam is between about one femtosecond and about ten nanoseconds.

7. The method of claim 1, wherein a frequency of the ultrasound waves is determined based on a size of the cavitation nucleus.

8. The method of claim 1, wherein the wavelength of the optical radiation is such that the first material is transparent to the optical radiation.

9. The method of claim 5, wherein the laser beam has a wavelength of between about 400 nm and about $2\mu$.

10. The method of claim 1, wherein the optical radiation is directed to the portion of the second material by a fiber optic probe.

11. The method of claim 10, wherein a sighting device is used to direct the fiber optic probe.

12. The method of claim 1, wherein the ultrasound waves are focused at or proximate to the cavitation nucleus.

13. The method of claim 1, wherein the ultrasound waves cause a permanent mechanical disruption in at most the portion of the second material and the first portion of the first material.

14. The method of claim 1, wherein the first portion of the first material is biological material and is substantially destroyed, and a second portion of the first material is not substantially destroyed.

15. The method of claim 1, further comprising introducing one of protein and lipids into the second material, the one of protein and lipids stabilizing the cavitation nucleus by surrounding the cavitation nucleus.

16. The method of claim 1, wherein the first material is a solid and the mechanical disruption in the first portion of the first material results in etching of a surface of the first material.

17. The method of claim 1, wherein the first material is the second material.

18. An apparatus for processing a first material, comprising:
    an optical radiation generator that generates focused optical radiation that creates a cavitation nucleus in a portion of a second material by subjecting the portion of the second material to the focused optical radiation; and
    an ultrasound transducer that generates ultrasound waves that cause the cavitation nucleus to explode, the explosion causing mechanical disruption in a first portion of the first material adjacent the cavitation nucleus.

19. The apparatus of claim 18, wherein the optical radiation creates the cavitation nucleus by causing optical breakdown of the portion of the second material.

20. The apparatus of claim 19, wherein the optical breakdown results in the ionization of the portion of the second material.

21. The apparatus of claim 18, wherein the optical radiation is sufficiently focused so that optical breakdown of only the portion of the second material occurs.

22. The apparatus of claim 18, further comprising an ultrasound focusing device that focuses the ultrasound waves at or proximate to the cavitation nucleus.

23. The apparatus of claim 18, wherein the ultrasound waves cause a permanent mechanical disruption in at most the portion of the second material and the first portion of the first material.

24. The apparatus of claim 18, wherein a frequency of the ultrasound waves is determined based on a size of the cavitation nucleus.

25. The apparatus of claim 18, wherein the wavelength of the optical radiation is such that the first material is transparent to the optical radiation.

26. The apparatus of claim 18, wherein the optical radiation is a short pulse duration laser beam.

27. The apparatus of claim 26, wherein the pulse duration of the laser beam is between about one femtosecond and about ten nanoseconds.

28. The apparatus of claim 26, wherein the laser beam has a wavelength of between about 400 nm and about $2\mu$.

29. The apparatus of claim 18, further comprising a fiber optic probe that directs the optical radiation to the portion of the second material.

30. The apparatus of claim 29, further comprising a sighting device for directing the fiber optic probe.

31. The apparatus of claim 18, further comprising an introduction tube that introduces one of protein and lipids into or proximate to the portion of the second material.

32. The apparatus of claim 18, further comprising a platform to which the optical radiation generator and the ultrasound transducer are mounted,
    wherein the first material is a body of water and the apparatus is for producing a cavitation signature in the body of water.

33. The apparatus of claim 18, wherein the apparatus is for etching a surface of a solid.

34. The apparatus of claim 18, wherein the first material is the second material.

35. An apparatus for processing a first material, comprising:
    means for creating a cavitation nucleus in a portion of a second material by focusing optical radiation on the portion of the second material; and
    means for causing mechanical disruption in a portion of the first material adjacent to the cavitation nucleus by subjecting the cavitation nucleus to ultrasound waves.

* * * * *